US 11,443,218 B2

(12) United States Patent
Gupta et al.

(10) Patent No.: US 11,443,218 B2
(45) Date of Patent: Sep. 13, 2022

(54) MODEL GUIDED DEEP LEARNING APPROACH TOWARDS PREDICTION OF PHYSICAL SYSTEM BEHAVIOR

(71) Applicants: Sandeep Gupta, Phoenix, AZ (US); Ayan Banerjee, Mesa, AZ (US)

(72) Inventors: Sandeep Gupta, Phoenix, AZ (US); Ayan Banerjee, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 938 days.

(21) Appl. No.: 16/226,461

(22) Filed: Dec. 19, 2018

(65) Prior Publication Data
US 2019/0188587 A1 Jun. 20, 2019

Related U.S. Application Data (60) Provisional application No. 62/608,535, filed on Dec. 20, 2017.

(51) Int. Cl.
*G06N 7/00* (2006.01)
*A61B 5/00* (2006.01)
(Continued)

(52) U.S. Cl.
CPC ........... *G06N 7/00* (2013.01); *A61B 5/14532* (2013.01); *A61B 5/7275* (2013.01);
(Continued)

(58) Field of Classification Search
CPC ........ G06N 3/08; G06N 3/048; G06N 3/0445; G06N 7/00; G06N 20/10; A61B 5/14532; A61B 5/7275
(Continued)

(56) References Cited

U.S. PATENT DOCUMENTS 9,424,084 B2  8/2016 Gupta et al.
9,619,213 B2  4/2017 Gupta et al.
(Continued)

FOREIGN PATENT DOCUMENTS

WO  2014018555 A1  1/2014
WO  2015095530 A1  6/2015

OTHER PUBLICATIONS

Alashkar et al., "Examples—Rules Guided Deep Neural Network for Makeup Recommendation." AAAI Conference on Artifical Intelligence, 2017, pp. 941-947.
(Continued)

*Primary Examiner* — Ted M Wang
(74) *Attorney, Agent, or Firm* — Michael Best & Friedrich LLP (57) ABSTRACT

Systems and methods are provided for controlling predictive medical monitoring. A non-linear-predictive-guide model estimates a patient parameter that is used as a guide in a deep neural network for improving accuracy of estimation by the deep neural network. The guide model generates a guiding first estimated patient parameter based on the guide model and patient input data. The deep neural network generates a second estimated patient parameter based on the deep neural network, the patient input data, and the guiding first estimated patient parameter. The deep neural network includes an input layer that receives the guiding first estimated patient parameter, and hidden layers including respective artificial neurons configured to perform a linear or nonlinear transformation on output of at least one artificial neuron from an adjacent layer in the deep neural network. An output layer receives at least one output from a hidden layer.

20 Claims, 5 Drawing Sheets

(51) Int. Cl.
  *A61B 5/145*   (2006.01)
  *G06N 3/08*    (2006.01)
  *G06N 20/10*   (2019.01)
  *G06N 3/04*    (2006.01)

(52) U.S. Cl.
  CPC ............ *G06N 3/0481* (2013.01); *G06N 3/08* (2013.01); *G06N 20/10* (2019.01); *G06N 3/0445* (2013.01)

(58) Field of Classification Search
  USPC .......................................................... 702/19
  See application file for complete search history.

(56) References Cited

U.S. PATENT DOCUMENTS

| | | |
|---|---|---|
| 9,626,521 B2 | 4/2017 | Gupta et al. |
| 9,642,543 B2 | 5/2017 | Banerjee et al. |
| 9,706,963 B2 | 7/2017 | Gupta et al. |
| 10,074,028 B2 | 9/2018 | Gupta et al. |
| 10,342,447 B2 | 7/2019 | Banerjee et al. |
| 2013/0317377 A1 | 11/2013 | Gupta et al. |
| 2014/0278333 A1 | 9/2014 | Gupta et al. |
| 2015/0261898 A1 | 9/2015 | Gupta et al. |
| 2015/0277410 A1 | 10/2015 | Gupta et al. |
| 2016/0313779 A1 | 10/2016 | Gupta et al. |
| 2018/0068083 A1* | 3/2018 | Cohen .................... G16B 50/30 |
| 2018/0103911 A1 | 4/2018 | Banerjee et al. |
| 2018/0189678 A1 | 7/2018 | Gupta et al. |
| 2018/0300487 A1 | 10/2018 | Gupta et al. |
| 2018/0301061 A1 | 10/2018 | Paudyal et al. |
| 2018/0344284 A1* | 12/2018 | Freudenberger ....... A61B 34/30 |
| 2019/0212803 A1 | 7/2019 | Gupta et al. |

OTHER PUBLICATIONS

Bergman et al., "Physiologic evaluation of factors controlling glucose tolerance in man: measurement of insulin sensitivity and beta-cell glucose sensitivity from the response to intravenous glucose", Journal of Clinical Investigation, vol. 68, No. 6, 1981, pp. 1456-1467, 1981.

Bojarski et al., "End to end learning for self-driving cars," arXiv preprint arXiv: 1604.07316, 2016.

Collobert et al., "A unified architecture for natural language processing: Deep neural networks with multitask learning," Proceedings of the 25th international conference on Machine learning. ACM, 2008, pp. 160-167.

Glorot et al., "Understanding the difficulty of training deep feed forward neural networks," Proceedings of the Thirteenth International Conference on Artificial Intelligence and Statistics, 2010, pp. 249-256.

Hovorka et al., "Nonlinear model predictive control of glucose concentration in subjects with type 1 diabetes," Physiological Measurement, vol. 25, No. 4, 2004, pp. 905-920.

Kalman et al., "A new approach to linear filtering and prediction problems," Journal of Basic Engineering, vol. 82, No. 1., 1960, pp. 35-45.

Kingma et al., "Adam: A method for stochastic optimization," ICLR 2015, pp. 1-15.

Kok, "Predicting blood glucose levels of diabetics using artificial neural networks," Research Assignment for Master of Science, Delft University of Technology, 2004, 49 pages.

Krizhevsky et al., "Imagenet classification with deep convolutional neural networks," Advances in Neural Information Processing Systems, 2012, pp. 1097-1105.

Mirshekarian et al., "Using LSTMs to learn physiological models of blood glucose behavior," Engineering in Medicine and Biology Society 39th Annual International Conference of the IEEE, 2017, pp. 2887-2891.

Pappada et al., "Neural network-based real-time prediction of glucose in patients with insulin-dependent diabetes," Diabetes Technology & Therapeutics, vol. 13, No. 2, pp. 135-141, 2011.

Parker et al., "A model-based algorithm for blood glucose control in type i diabetic patients," IEEE Transactions on Biomedical Engineering, vol. 46, No. 2, pp. 148-157, 1999.

Perez-Gandia et al., "Artificial neural network algorithm for online glucose prediction from continuous glucose monitoring," Diabetes Technology & Therapeutics, vol. 12, No. 1, pp. 81-88, 2010.

Sparacino et al., "Glucose concentration can be predicted ahead in time from continuous glucose monitoring sensor time-series," IEEE Transactions on Biomedical Engineering, vol. 54, No. 5, pp. 931-937, 2007.

Tresp et al., "Neural-network models for the blood glucose metabolism of a diabetic," IEEE Transactions on Neural networks, vol. 10, No. 5, pp. 1204-1213, 1999.

Van Riel, "Minimal models for glucose and insulin kinetics—a Matlab implementation," Eindhoven University of Technology, 2004, 23 pages.

Wang et al., "Multiple linear regression and artificial neural network to predict blood glucose in overweight patients," Experimental and Clinical Endocrinology & Diabetes, vol. 124, No. 1, pp. 34-38, 2016.

Zainuddin et al., "A neural network approach in predicting the blood glucose level for diabetic patients," International Journal of Computational Intelligence, vol. 5, No. 1, pp. 72-79, 2009.

Zecchin et al., "How much is short-term glucose prediction in type 1 diabetes improved by adding insulin delivery and meal content information to CGM data? A proof-of-concept study," Journal of Diabetes Science and Technology, vol. 10, No. 5, pp. 1149-1160, 2016.

U.S. Appl. No. 16/413,018.
U.S. Appl. No. 16/593,337.

* cited by examiner

Table 4
RMSE For Model Guided Neural Networks NN Model I and II

|  | NN Model I | | | | NN Model II | | | | NN Model III | | | | Guided SVR | | | |
|---|---|---|---|---|---|---|---|---|---|---|---|---|---|---|---|---|
|  | CM-I | CM-II | CM-III | CM-IV | CM-I | CM-II | CM-III | CM-IV | CM-I | CM-II | CM-III | CM-IV | CM-I | CM-II | CM-III | CM-IV |
| P1 | 0.075 | 0.053 | 0.049 | 0.045 | 0.1008 | 0.076 | 0.0552 | 0.0511 | 0.0176 | 0.017 | 0.01 | 0.00293 | 0.428 | 0.241 | 0.164 | 0.169 |
| P2 | 0.006 | 0.307 | 0.057 | 0.067 | 0.1219 | 0.2139 | 0.0883 | 0.0304 | 0.0113 | 0.198 | 0.039 | 0.0028 | 0.231 | 0.054 | 0.043 | 0.044 |
| P3 | 0.017 | 0.2635 | 0.08 | 0.056 | 0.086 | 0.269 | 0.025 | 0.0539 | 0.0205 | 0.238 | 0.011 | 0.00909 | 0.335 | 0.157 | 0.138 | 0.154 |
| P4 | 0.085 | 0.139 | 0.047 | 0.082 | 0.1313 | 0.1692 | 0.0638 | 0.0610 | 0.0132 | 0.0857 | 0.012 | 0.00879 | 0.417 | 0.273 | 0.256 | 0.240 |
| P5 | 0.04 | 0.307 | 0.031 | 0.031 | 0.0513 | 0.2056 | 0.0451 | 0.0356 | 0.0174 | 0.2055 | 0.0063 | 0.0053 | 0.369 | 0.174 | 0.162 | 0.167 |
| P6 | 0.01 | 0.07 | 0.021 | 0.0114 | 0.081 | 0.07 | 0.024 | 0.0273 | 0.0165 | 0.05 | 0.0148 | 0.0053 | 0.376 | 0.219 | 0.204 | 0.194 |
| P7 | 0.02 | 0.018 | 0.018 | 0.0218 | 0.051 | 0.05 | 0.023 | 0.021 | 0.0174 | 0.25 | 0.07 | 0.0019 | 0.451 | 0.231 | 0.16 | 0.091 |

MODEL GUIDED DEEP LEARNING APPROACH TOWARDS PREDICTION OF PHYSICAL SYSTEM BEHAVIOR

CROSS REFERENCE TO RELATED APPLICATIONS

This application claims the benefit of U.S. Provisional Patent Application No. 62/608,535, filed on Dec. 20, 2017, which is hereby incorporated by reference in its entirety.

BACKGROUND

Cyber-physical control systems are being used in many critical infrastructures including smart grids, medical systems, and autonomous vehicles. An important feature of such control systems is that a controller algorithm interacts with a physical system through sensing and actuation. A popular method used for developing a controller strategy for these systems is model predictive control. In such a strategy, a model of the physical system is used to obtain an estimation of the state variables that can accurately describe the physical system at a given time in the future. The prediction is then used in the decision algorithm of the controller. Often the prediction model may not accurately represent the practical deployment of the system. In such cases, the prediction model will be inaccurate and it can lead to wrong decisions made by the controller.

A case in point is that of closed loop blood glucose control systems or artificial pancreas where parameters for controlling the artificial pancreas are based on estimated blood glucose levels. In a closed loop blood glucose control system also known as Artificial Pancreas (AP), there is a Continuous Glucose Monitor (CGM) sensor that senses blood glucose levels every 5 minutes. The current blood glucose level is used by the controller to predict the blood glucose level 30 minutes in the future. The predictive model is the Bergman minimal model that characterizes the estimated glucose insulin dynamics within the human body. Based on the predicted blood glucose level the infusion pump computes the current insulin infusion rate. The closed loop blood glucose control system may use the Bergman minimal model to estimate the future blood glucose level of a person based on the current measurements of blood glucose, blood insulin, and interstitial insulin levels. In addition to inaccuracies, the physical system prediction models also require personalization. This involves evaluation of controller parameters and correct configuration to match the operation of the specific physical system instance. Such personalizations can only be obtained by observing the control system and utilizing the input output data. Hence, data driven approaches such as machine learning techniques can potentially be utilized to iteratively improve a physical model.

Over the years, various types of algorithms have been applied towards the prediction of blood glucose levels and hyper- and hypoglycemic events. A first-order polynomial model and also an auto-regressive model have been used to describe a time series obtained from a continuous glucose monitor (CGM). Using model predictive controllers (MPCs) in conjunction with a Kalman Filter, hyperglycemic and hypoglycemic events in a similar time series have been predicted. More recently, various types of neural networks have been used to predict both blood glucose levels. A Long Short Term Memory (LSTM) based recurrent neural network has been used to predict the blood glucose levels in Type 1 Diabetes patients. Using artificial neural networks and multiple linear regression, blood glucose levels have been predicted in overweight patients. Studies have also examined the effects of adding meal content information and insulin delivery towards the prediction of short term blood glucose prediction.

SUMMARY

In machine learning, neural networks are essentially computer models that are structured based on biological neural networks and are used to, through a learning process, estimate unknown functions that are dependent on a large number of inputs. Neural networks are basically an assembly of interconnected "neurons" that exchange messages between one another. Each of the connections between the neurons has a specific numeric weight that can be fine-tuned through a learning process based on various inputs and considering various outputs. Eventually the numeric weights can be sufficiently tuned to provide correct outputs. The tuning of these numeric weights is often times referred to as training the neural network. A better trained neural network provides more accurate results. This concept allows neural networks to be capable of learning and adapting to various inputs, including previously unseen inputs.

There are many applications for neural networks, some of which include visual recognition and classification (e.g., pattern recognition) as well as speech recognition. For example, a neural network for visual recognition can include a set of input neurons which may be activated by an input image. For example, for an input image that is a color image including 64 pixels (e.g., an 8-by-8 pixel image), each of the input neurons can be activated using the red, blue green (RGB) values of a particular pixel of the 64 pixels of an input image. After being weighted and transformed by a function, the activations (i.e., outputs) of the neurons of one "layer" are then passed on to other neurons of another "layer." This process is repeated through all of the intermediary layers of the neural network until finally, an output neuron of an output layer determines which type of image was input. A neural network that has one intermediary layer is typically considered to be a shallow neural network and a neural network having two or more intermediary layers is considered a deep neural network that can perform deep learning.

Deep neural networks are a more recent development and have been applied successfully in the fields of image classification, in natural language processing and also self-driving cars. Guided deep learning uses a guide to enhance the representation learning capabilities of neural networks and is capable of producing more accurate results.

A new type of guided deep learning is disclosed, one that uses a model to help the deep neural network learn the underlying representation. As described herein, this guide model is a complex non-linear physiological model. This model guided deep learning neural network method is applied to learn the underlying representation in a dataset that is based on a non-linear physiological model. The model guided deep learning network developed is compared with three other types: a single layer neural network, a wide neural network, and a deep neural network; and shows that using the model guided deep learning version makes the predictions in this domain more accurate. In addition to the aforementioned neural networks, the performance of the model guided deep learning neural network is compared with that of a guided Support Vector Regression. The disclosed model guided deep learning network can be applied to datasets whose underlying representations are based on non-linear models.

In some embodiments, a control system for a predictive medical monitoring comprises an electronic processor and a memory communicatively coupled to the electronic processor. The memory stores a guide model including a non-linear predictive model for estimating a guiding first patient parameter and a deep neural network. The deep neural network includes an input layer configured to receive the guiding first estimated patient parameter and a plurality of hidden layers. Each hidden layer comprises a respective plurality of artificial neurons and each artificial neuron in a hidden layer is configured to perform a linear or nonlinear transformation on output of at least one artificial neuron from an adjacent layer in the deep neural network. The memory further stores an output layer configured to receive at least one output from a hidden layer. The memory further stores instructions that when executed by the electronic processor configure the electronic processor to receive patient input data and input the patient input data into the guide model and generate the guiding first estimated patient parameter based on the guide model and the patient input data. The electronic processor is further configured to input the patient input data and the guiding first estimated patient parameter into the deep neural network input layer and generate the second estimated patient parameter based on the deep neural network, the patient input data, and the guiding first estimated patient parameter.

In some embodiments, a method for controlling a predictive medical monitor comprises storing, in a memory, a guide model including a non-linear predictive model for estimating a guiding first patient parameter. Also stored in the memory is a deep neural network where the deep neural network includes an input layer configured to receive the guiding first estimated patient parameter, and a plurality of hidden layers. Each hidden layer comprises a respective plurality of artificial neurons and each artificial neuron in a hidden layer is configured to perform a linear or nonlinear transformation on output of at least one artificial neuron from an adjacent layer in the deep neural network. The deep neural network further includes an output layer configured to receive at least one output from a hidden layer. An electronic processor that is coupled to the memory receives patient input data, inputs the patient input data into the guide model and generates the guiding first estimated patient parameter based on the guide model and the patient input data. The electronic processor further inputs the patient input data and the guiding first estimated patient parameter into the deep neural network input layer and generates the second estimated patient parameter based on the deep neural network, the patient input data, and the guiding first estimated patient parameter.

In some embodiments, a computer-readable medium comprises instructions that when executed by an electronic processor cause the electronic processor to store, in a memory, a guide model including a non-linear predictive model for estimating a guiding first patient parameter. The electronic processor further stores, in the memory, a deep neural network, the deep neural network including an input layer configured to receive the guiding first estimated patient parameter and a plurality of hidden layers. Each hidden layer comprises a respective plurality of artificial neurons, and each artificial neuron in a hidden layer is configured to perform a linear or nonlinear transformation on output of at least one artificial neuron from an adjacent layer in the deep neural network. The deep neural network further includes an output layer configured to receive at least one output from a hidden layer. The electronic processor further receives patient input data. The electronic processor further inputs the patient input data into the guide model and generates the guiding first estimated patient parameter based on the guide model and the patient input data. The electronic processor further inputs the patient input data and the guiding first estimated patient parameter into the deep neural network input layer and generates the second estimated patient parameter based on the deep neural network, the patient input data, and the guiding first estimated patient parameter.

In some embodiments, a control system for predictive medical monitoring comprises a computer processor, a deep neural network, and a guide model configured to generate an estimation of a patient parameter and to input the estimated parameter to the deep neural network. The deep neural network comprises the input layer configured to receive the estimated parameter, a plurality of hidden layers, and an output layer. Each hidden layer comprises a respective plurality of nodes where each node in a hidden layer is configured to perform a linear or nonlinear transformation on output of at least one node from an adjacent layer in the deep neural network. The plurality of hidden layers have parameters corresponding thereto. Values of the parameters are based upon the estimated parameter, and the output layer provides a prediction value of the patient parameter. The guide model may be a physiological model. The physiological model may be a Bergman Minimal Model. The patient parameter may be a blood glucose level.

Other aspects of the disclosure will become apparent by consideration of the detailed description and accompanying drawings.

DETAILED DESCRIPTION

Before any embodiments of the disclosure are explained in detail, it is to be understood that the disclosed methods and systems are not limited in their application to the details of construction and the arrangement of components set forth in the following description or illustrated in the following drawings. The disclosed methods and systems are capable of other embodiments and of being practiced or of being carried out in various ways.

Cyber-physical control systems involve a discrete computational algorithm to control continuous physical systems. Often the control algorithm uses predictive models of the physical system in its decision making process. However, physical system models suffer from several inaccuracies when employed in practice. Mitigating such inaccuracies is often difficult and physical system models may have to be redone for different instances of the physical system. A model guided deep learning method is disclosed for extraction of accurate prediction models of physical systems in the presence of artifacts observed in real life deployments. Given an initial potentially suboptimal mathematical prediction model, the model guided deep learning method iteratively improves the model through a data driven training approach. The disclosed approach is applied to the closed loop blood glucose control system. Using this disclosed approach the blood glucose level prediction accuracy is improved 100 times with respect to simply using the Bergman Minimal model.

In an artificial neural network an artificial neuron is a computational model that attempts to mimic the computational capability of biological neurons. An artificial neuron takes in a set of inputs and outputs a single value after performing a non-linear transform on the inputs. The mathematical representation of an artificial neuron is shown below:

$$y(x) = \sigma\left(\sum_{i=1}^{n} w_i x_i\right),$$

where y(x) is regarded as the output axon of the neuron x with n input dendrites $x_1, \ldots, x_n$. Each input dendrite is weighted by a weight $w_i$ and $\sigma$ is called the activation function which is essentially a threshold function that denotes whether the neuron fired or not for the given set of inputs. By means of the activation function non-linearity is introduced to the output of these artificial neurons. Neurons are stacked to form layers and there exist interconnections between these layers and sometimes within each layer as well. A combination of these layers of artificial neurons forms an artificial neural network (ANN).

Two important design choices for creating an ANN include determining the number of layers and the number of neurons needed per layer. The layers in an ANN are as follows: an input layer which consists of neurons that are fed as inputs to the ANN, a set of hidden layers which are responsible for approximating the computable function, and an output layer comprised of one or more neurons that represent the output of the function under consideration. It is noted that by increasing the number of hidden layers in an ANN the non-linearity of the ANN is increased which allows it to approximate highly non-linear functions. Neural networks with multiple hidden layers are termed deep neural networks.

Cyber-physical systems often use predictive models of the physical system for the decision making process. Although these predictive models may be theoretically sound, when applied in practice they may suffer from various inaccuracies which in turn degrades the performance of the system as a whole. Dealing with these inaccuracies in the implementation of predictive models is a complex task since the physical system is usually dependent on a large number of parameters. Instead of dealing with several different instances of the physical system and trying to resolve issues for each of them, the disclosed model guided deep neural network system provides a way to increase the glucose level prediction accuracy of suboptimal predictive models in the presence of artifacts in practice. These artifacts can include physical activity that changes insulin sensitivity of the subject, or error in reporting meal amount or any natural variation in the physiological parameters of the subject.

The predictive models used in cyber-physical systems are highly non-linear by nature. Since neural networks are capable of approximating non-linear computable functions, a neural network is used to extract prediction models using a data driven approach. A deep neural network is utilized since the added number of hidden layers allows it to learn the underlying non-linear representation more efficiently and with a higher level of precision. Instead of allowing the deep neural network to freely learn from the data and extract models, the deep neural network is provided with a guide in the form of the predictive model. This guide model must be integrated with the deep neural network. In this disclosure, the predictive model is integrated into the deep neural network as an additional input feature for the network. For each sample of input features, the predictive model is used to generate an estimated value for the parameter that needs to be predicted. The estimate generated by the predictive model for each sample in the input data is a result of processing that sample using a mathematical model and hence captures the non-linearity of the predictive model. This estimated value is then added as an additional input feature for the deep neural network. The estimate of the parameter from the predictive model aids the deep neural network in learning only those parameters that are significant for correctly approximating the underlying model.

Usage of this disclosed model guided deep learning is applied to the closed loop glucose control system for T1DM patients. The predictive model used as the guide for the disclosed deep neural network is a physiological model called the Bergman Minimal Model. In some embodiments, the existing Bergman Minimal Model is improved upon, and this modified version is utilized as the guide.

Figure 1:
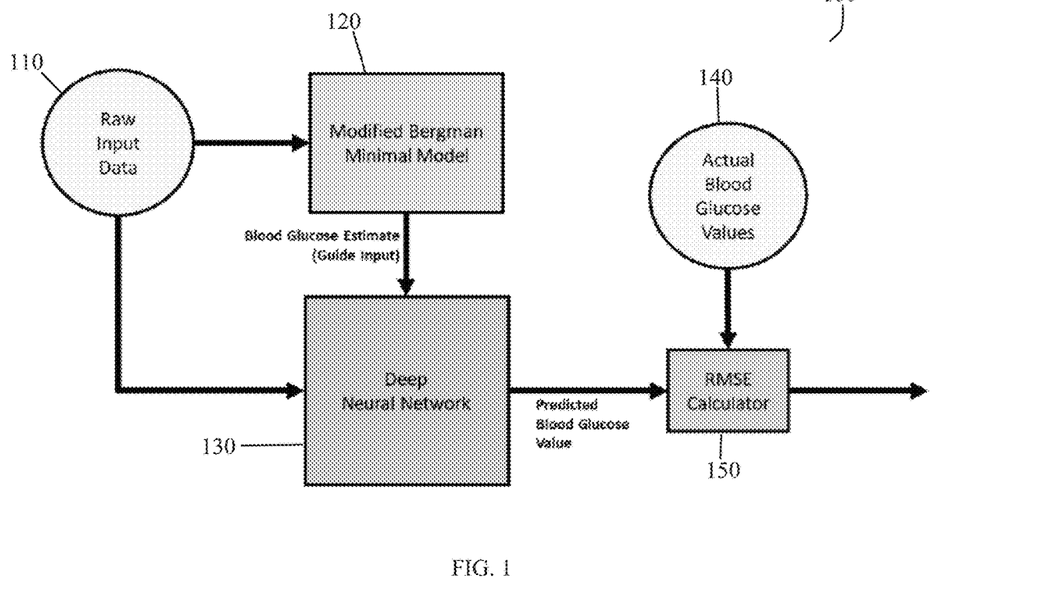
FIG. 1 is a block diagram depicting architecture for guided deep learning using a predictive physiological model as a guide, in accordance with some embodiments.

FIG. 1 represents an overall architecture for model guided deep learning using a predictive physiological model as a guide, as applied to the prediction of blood glucose levels in T1DM patients. FIG. 1 includes a system 100, a raw input data 110, a predictive physiological model 120, a deep neural network 130, measured physiological data 140, and a root mean squared calculator 150. The predictive physiological model 120 may be referred to as a guide model. In some embodiments, the predictive physiological model 120 may be modified Bergman minimal model.

The system 100 may be utilized to predict future blood glucose levels. In such embodiments, the raw input data 110 may include data that represents a patient's measured plasma glucose. Plasma insulin and interstitial insulin in the blood may also be included in the raw data input 110. In some embodiments, the raw input data 110 may include one or more additional factors, for example, an endogenous glucose production factor, a physical activity factor, and a meal intake factor.

The predictive physiological model 120 may receive the raw input data 110 and output a first estimated future blood glucose level. The deep neural network 130 may receive the raw input data 110 and the first estimated future blood glucose level from the predictive physiological model 120. The deep neural network 130 may utilize the first estimated future blood glucose level as a guide and estimate a second estimated future blood glucose level based on the raw input data 110 and the guide. Results from the deep neural network 130 may be tested in the root mean squared error calculator 150 based on the second estimated future blood glucose levels and actual blood glucose measurements 140 that are taken at the times corresponding to the estimates. Moreover, the second estimated future blood glucose levels output from the deep neural network 130 may be utilized to determine input to a closed loop control system, such as an artificial pancreas to determine parameters for controlling dosage of a patient's insulin or other substances.

Figure 2:
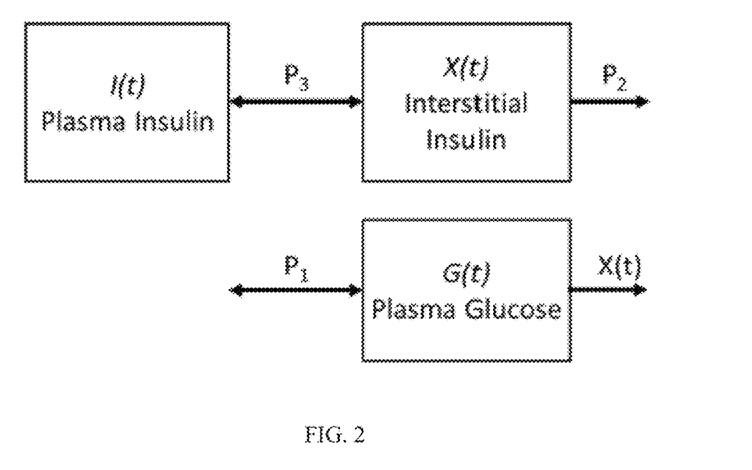
FIG. 2 illustrates a two compartment Bergman Minimal Model, in accordance with some embodiments.

Glucose models are used to study type 1 diabetes mellitus. The model currently mostly used to research on the metabolism of glucose and insulin regulation is the Bergman minimal model. This model was proposed for the interpretation of glucose and insulin dynamics. The Bergman Minimal Model is a two compartment model: one model for glucose disappearance and the other model for insulin kinetics. FIG. 2 illustrates the two compartment Bergman Minimal Model. FIG. 2 shows the minimal model for glucose disappearance and the minimal model for insulin kinetics.

The equations describing the minimal model are given below—

$$\frac{dG(t)}{dt} = k_1(G_b - G(t)) - X(t)G(t), \ G(t_0) = G_0,$$

$$\frac{dX(t)}{dt} = k_2(I(t) - I_b) - k_3 X(t), \ X(t_0) = 0$$

$t_0$ is the time of the glucose injection, G(t) is the plasma glucose concentration[mg/dL], I(t) is the plasma insulin level[µU/mL], and X(t) is the interstitial insulin activity. In order to improve blood glucose prediction in the original minimal model, physical activity factor was added along with the inclusion of endogenous glucose production (EGP). Insulin sensitivity is linearly and very tightly associated to the EGP sensitivity. So in order to quantify the effects of interstitial insulin on the endogenous production of glucose, the EGP is accumulated with X(t). By adding these two extra factors along with the meal intake, a more accurate way of simulating the dynamics of insulin was ensured.

As shown in FIG. 2, the Bergman minimal model is a two compartmental model, the interstitial insulin compartment and the plasma compartment. $p_1$, $p_2$, $p_3$ are rate constants that express the diffusion rates of insulin and glucose in between the two compartments.

This modified Bergman Minimal Model is used as a guide model 120 and input to the neural networks 130 shown in FIG. 1. This modified implementation of the Bergman Minimal Model is implemented as a preprocessing step for the dataset 110 and then fed to the neural networks 130 as the guide input.

In order to evaluate methods for model guided deep learning using a predictive physiological model as a guide, the original Bergman Minimal Model and the modified Bergman Minimal Model were implemented in MATLAB. The data for each patient was run through both of these implementations and an estimate of the blood glucose level was obtained using these models.

Three variants of neural networks are used: a single layer neural network (NN-Model I), a single wide layer neural network (NN-Model II), and a deep neural network (NN-Model III). Table 1 includes the details of each type of neural network used.

TABLE 1

Neural Network Details

| Name | Hidden Layers | Hidden Layer Neurons |
|---|---|---|
| NN-Model I | 1 | 5 |
| NN-Model II | 1 | 500 |
| NN-Model III | 11 | 50-80 |

For all three models of neural networks there are four input neurons and one output neuron. Additionally, the activation function for the hidden layer neurons is chosen to be the tan hyperbolic function and that for the output layer is the linear activation function. Mean squared error is used as the loss function and the Adam optimizer. The initial weight distribution for the neurons is the tan hyperbolic function. A batch size of 10 is used for all the neural network models. The learning rate was set to 0.001 and the epsilon value was set to $10^{-8}$.

The modified Bergman minimal model and its effect on the estimation of blood glucose levels are tested using four different variants of the disclosed guide model. In order to create each of the four different guide models one or more input features was added or removed from the modified Bergman Minimal Model implementation and the same feature(s) was added or removed from the input to the neural network it was fed into. The four variants of the guide model are listed in Table II. Henceforth each guide model will be referred to as seen in Table II.

Guided Support Vector Regression (SVR) using the guide models from Table II are also used to predict the blood glucose values. The predictions made using this guided SVR approach is compared and contrasted in the results and discussion sections.

TABLE 2

Guide Model and the Corresponding Model Variant upon Which It Is Based

| Guide Model No. | Guide Input Defined by |
|---|---|
| GM-I | Bergman Minimal Model |
| GM-II | Bergman Minimal Model with the effect of Endogenous Glucose Production |
| GM-III | Bergman Minimal Model with the effect of physical activity |
| GM-IV | Bergman Minimal Model with the effect of Endogenous Glucose Production & physical activity |

Training and testing of each of the aforementioned algorithms was done on a per patient basis. For each patient, the training dataset was composed of six days' worth of data and then testing was done on the remaining day of data, split into twelve hour sets. Each patient dataset was subject to each of the guide models mentioned in Table II above and then the data was input to each of the NN-Models with and without the model guide for training and testing.

The metric chosen for evaluating the different prediction algorithms was Root Mean Squared Error (RMSE). The RMSE is computed for each of the tested algorithms using the formula given below:

$$RMSE = \sqrt{\frac{1}{N}\sum_{I=1}^{N}(BG_{actual} - BG_{predicted})^2}$$

To evaluate the Bergman Minimal Model and the modified Bergman Minimal Model estimators the same formula is used for RMSE as mentioned above. The performance of a predictor (or estimator) in this paper is determined by observing the RMSE values for the predictions made. Since the dataset had been normalized prior to training and testing, an RMSE value closer to zero indicates a more accurate prediction of blood glucose levels.

Since blood glucose level predictions depend on biological parameters that vary from person to person, the data was collected, trained and tested on an individual basis. The dataset comprises of T1DM patient data collected from seven patients over a period of seven days. The CGM device collects blood glucose data every five minutes. A 16G accelerometer attached to the waist of each patient recorded their physical activity levels throughout the day and was also set to collect data every five minutes. Insulin sensitivity, basal and bolus rates and the EGP rate was determined for each patient individually and then recorded. The estimated blood glucose level from the modified Bergman Minimal Model is also fed as an input to the deep neural network. This dataset is standardized to zero mean and unity standard deviation. This was done to ensure a uniform scale among all the collected features and also to ensure that the deep neural network reached convergence faster.

In this section the results of all the experiments are presented and as demonstrated, the disclosed model guided deep learning neural network outperforms the existing methods of predicting blood glucose levels in T1DM patients.

In Table 3, the Bergman Minimal Model and the modified Bergman Minimal Model provide estimates of the blood glucose levels with high RMSE values. By accounting for meal intake, physical activity, and EGP, the modified Bergman Minimal Model performs slightly better in estimating the blood glucose levels as compared to the original minimal model.

Figure 3:
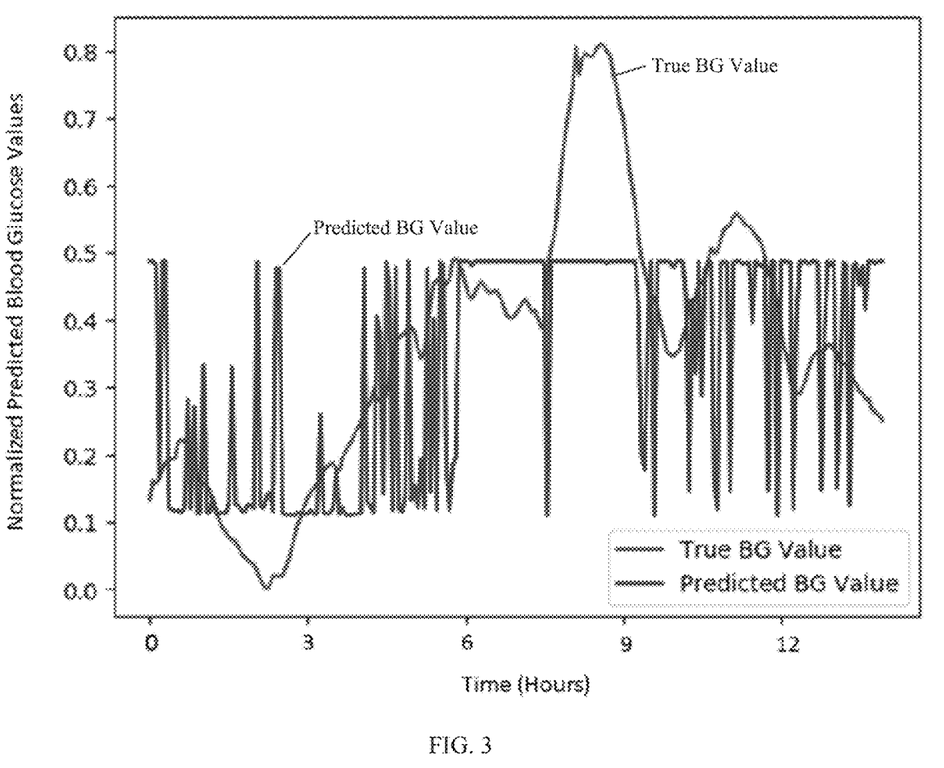
FIG. 3 graphically illustrates actual and predicted values of blood glucose for patient 5 using NN-Model III and no guide model input, in accordance with some embodiments.

Table 3 also evaluates the three neural network models NN-Models I, II and III when they are not provided with any guide input. The RMSE values obtained for each of the three NN-Models for the seven patients are also shown in Table 3. It is to be noted that the deep neural network, which is NN-Model III, has the lowest RMSE values for most of the test cases. This can be attributed to the increased non-linearity of NN-Model III due to the increased number of hidden layers and thus it is able to learn the non-linearity of the underlying model better. FIG. 3 graphically illustrates actual and predicted values of blood glucose for patient 5 using NN-Model III and no guide model input. As shown in FIG. 3, the learned representation does not result in accurate predictions.

TABLE 3

RMSE for Bergman Minimal Model, Modified Bergman Minimal Model, and No guide input NN Models I-III

| Patient | BERGMAN MINIMAL MODELS | | NN-MODELS I-III without guide input | | |
|---|---|---|---|---|---|
| | MODIFIED BMM | BMM | NN-Model I | NN Model II | NN-Model III |
| P1 | 0.422 | 0.461 | 0.54 | 0.45 | 0.38 |
| P2 | 0.387 | 0.450 | 0.36 | 0.44 | 0.45 |
| P3 | 0.527 | 0.476 | 0.45 | 0.68 | 0.31 |
| P4 | 0.467 | 0.513 | 0.33 | 0.42 | 0.43 |
| P5 | 0.447 | 0.573 | 0.47 | 0.32 | 0.60 |
| P6 | 0.442 | 0.488 | 0.66 | 0.54 | 0.26 |
| P7 | 0.425 | 0.477 | 0.32 | 0.65 | 0.55 |

On applying the four variants of the guide model to the NN-Models I, II and III, the prediction RMSE value is always lower as compared to using the NN-Models without a guide. Performance of the single layer neural network NN-Model I increases significantly (lowered RMSE values) and we can see that it is able to learn the underlying representation more accurately than without the guide input.

Figure 5:
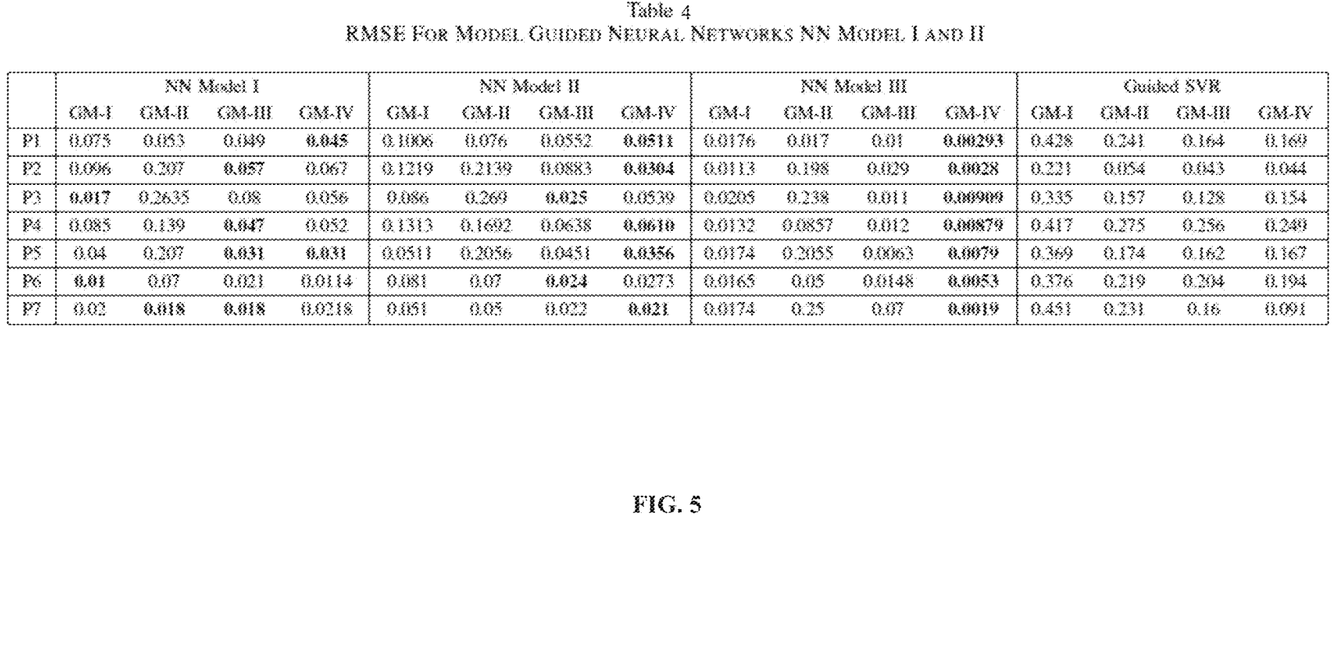
FIG. 5 includes Table 4 that represents root mean squared error (RMSE) data for model guided neural networks and guided support vector regression (SVR), in accordance with some embodiments.

Table 4 is shown in FIG. 5. Table 4 includes RMSE data for model guided neural networks including NN model I, II, and III, and guided SVR. From Table 4, the RMSE values indicate that the NN-Model I outperforms the Bergman Minimal Model estimator and the guided SVR for most cases. It however has varied performance across with respect to the four guide models used. Using NN-Model II with the four guide models results in RMSE values (refer to the table values in FIG. 5 that are not always lower than those obtained for NN-Model I). Since NN-Model II is also composed of only a single hidden layer but with a much larger number of neurons in it, the network may be learning the insignificant parameters more than NN-Model I.

The table in FIG. 5 also shows the RMSE values for the predictions made by the model guided SVR using the guide models from Table 2. The predictions made by the guided SVR were also observed to be more accurate than the estimates obtained using only the physiological models. GM-IV model used as a guide to the SVR produces the lowest prediction error in most cases.

The Table 4 shown in FIG. 5 also indicates the RMSE values for each variant of the guide model when passed to NN-Model III for prediction. For all the cases NN-Model III when combined with GM-IV has the lowest RMSE values and can predict the blood glucose levels better than the other guide models for this type of neural network model. The decrease in the RMSE values for prediction using NN-Model III can be accounted for by the increased number of hidden layers present. The extra hidden layers allow NN-Model III to better understand the non-linearity of the physiological model used here and this when combined with the guide, NN-Model III learns the required representation better than without the guide input.

From the results described above, it has been demonstrated that the disclosed approach of model guided deep learning is able to significantly lower the prediction errors as compared to using only the predictive model or a free learning deep neural network. When applying the disclosed approach to a closed loop glucose control system for prediction of blood glucose levels, a significant improvement was seen in the predictions made for each patient. The guide model used for deep neural network is the modified Bergman Minimal Mode. Compared to the Bergman Minimal Model and modified Bergman Minimal Model being used individually to estimate blood glucose level for the dataset, the disclosed approach has an improvement in the RMSE values by a factor of almost 100. The disclosed approach improves on the RMSE values on an average by a factor of almost 50 when compared to a deep neural network without any guide, and by a factor of 32 when compared to using a guided SVR approach. Therefore, the disclosed guided approach improves the accuracy of the neural network of the neural network output.

For NN-Model III, the RMSE values obtained on the test sets for each patient is always much less when using a model guide as compared to without using the guide. In spite of having the same architecture of the deep neural network, the model guided deep neural network makes more accurate predictions.

Figure 4:
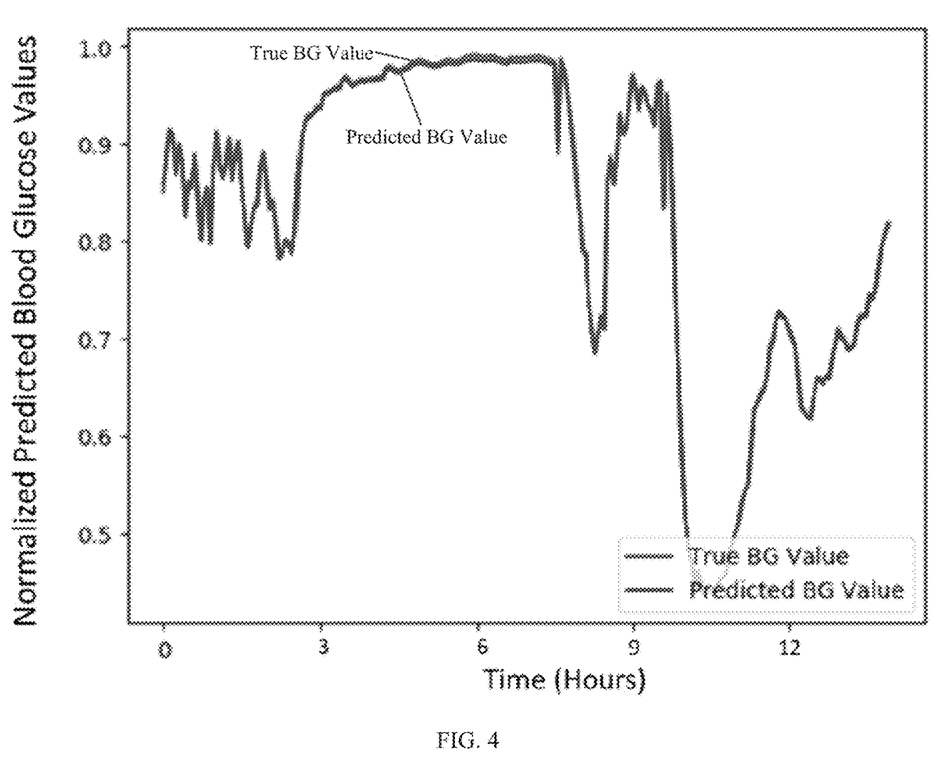
FIG. 4 graphically illustrates actual and predicted values of blood glucose using NN-Model III and GM-IV, in accordance with some embodiments.

FIG. 4 graphically illustrates actual and predicted values of blood glucose using NN-Model III and GM-IV. FIG. 4 shows the predictions made by the deep neural network NN-Model III for the best model guide GM IV. FIG. 5 (Table 4) shows the RMSE of the prediction results for all four model guides (GM I-IV) for Patient 1. As observed, the most accurate predictions are made by using GM-IV, i.e. the modified Bergman Minimal Model as the guide input. The quality of the predictive model used as the guide impacts the predictions made by the deep neural network. In this regard when the original physiological model (GM-I) is improved by adding the effects of EGP (GM-II) and the effects of physical activity (GM-III) and then combining both (GM-IV) the predictions made by the model guided deep neural network become increasingly closer to the ground truth values. Therefore, in conclusion, by introducing a model based guide to the free learning deep neural network, significant improvement to the predictions are made by the deep neural network.

A new form of guided deep learning using models as a guide for extraction of prediction models of physical systems is disclosed herein. The model guided deep learning method is applied to predict blood glucose levels in T1DM patients, and uses a modified Bergman Minimal Model as the physiological model to guide the deep neural network. Application of the disclosed approach to the closed loop glucose control in T1DM patients provided more accurate predictions as compared to using only the predictive models or deep neural network.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially generated propagated signal, e.g., a machine-generated electrical, optical, or electromagnetic signal, which is generated to encode information for transmission to suitable receiver apparatus for execution by a data processing apparatus. The computer storage medium can be a machine-readable storage device, a machine-readable storage substrate, a random or serial access memory device, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs that configure the computer to perform the disclosed functions by operating on input data and generating output. The processes and logic flows can also be performed by, and apparatus can also be implemented as, special purpose logic circuitry, e.g., an FPGA (field programmable gate array), an ASIC (application specific integrated circuit), a GPGPU (General purpose graphics processing unit), or some other type of processor.

Figure 6:
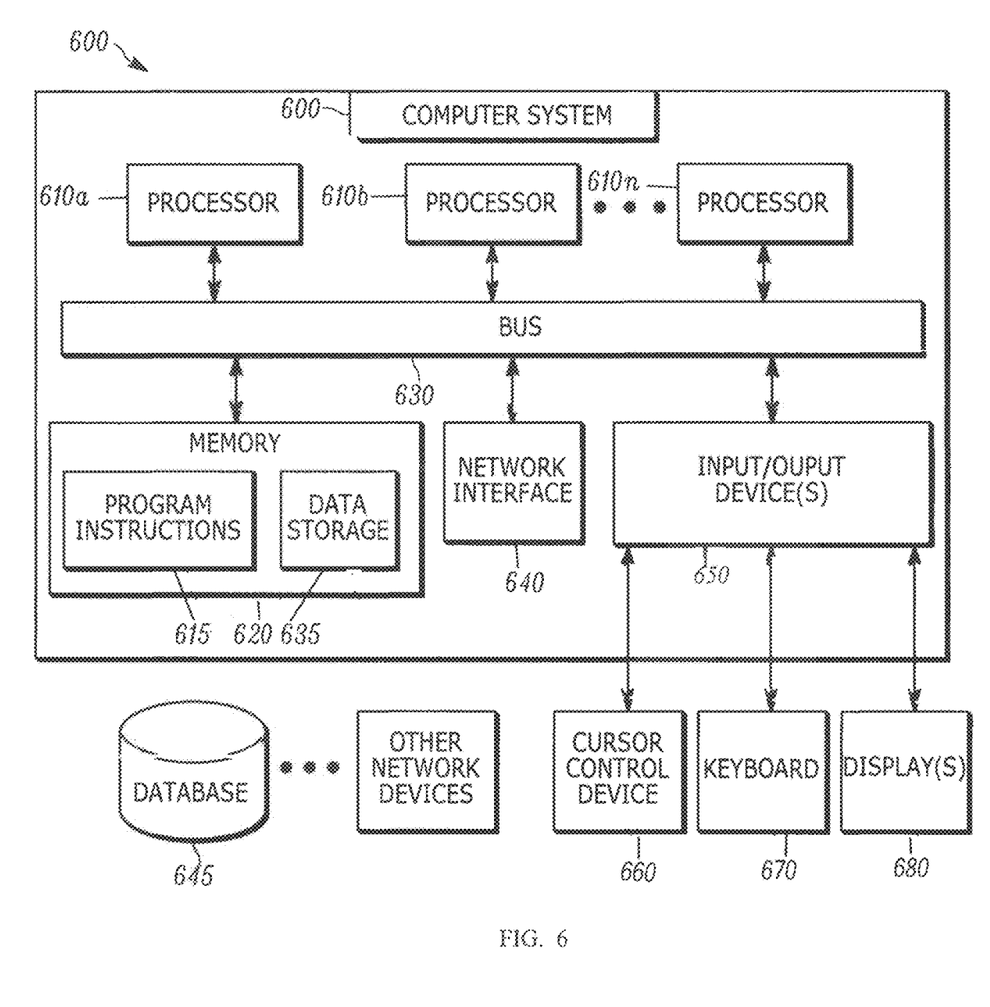
FIG. 6 is a block diagram of a computer system that is configured for implementing a model guided deep neural network, in accordance with some embodiments.

FIG. 6 is a block diagram of a computer system that is configured for implementing a model guided deep neural network to improve the prediction capability of predictive models in the presence of artifacts in practice. Examples of artifacts include physical activity that influences the insulin sensitivity, meal intake, and other natural variations in physiological parameters. As described above and in the attached figures, the model guided deep learning method iteratively improves the model through a data driven training approach.

Embodiments of the disclosure as described herein may be executed on one or more computer systems, which may interact with various other devices. One such computer system is illustrated by FIG. 6. In various embodiments, computer system 600 may include a personal computer system, desktop computer, laptop, notebook, mainframe computer system, smart phone, workstation, network computer, medical testing device, a handheld device, application server, or another type of computing or electronic device. The computer system 600 may be configured to implement the architecture for model guided deep learning using a predictive physiological model as a guide, as shown in FIG. 1, for example.

In the illustrated embodiment, computer system 600 includes one or more electronic processors 610 coupled to a system memory 620 via a bus 630. Computer system 600 further includes a network interface 640 coupled to the bus 630, and one or more input/output devices 650, such as cursor control device 660, keyboard 670, and display(s) 680. In some embodiments, it is contemplated that embodiments may be implemented using a single instance of computer system 600, while in other embodiments multiple such systems, or multiple nodes making up computer system 600, may be configured to host different portions or instances of embodiments.

In various embodiments, computer system 600 may be a uniprocessor system including one electronic processor 610, or a multiprocessor system including several electronic processors 610 (e.g., two, four, eight, or another suitable number). Electronic processors 610 may each be a suitable processor capable of executing instructions. For example, in various embodiments, electronic processors 610 may be operable to implement a variety of instruction set architectures (ISAs). In some embodiments, at least one electronic processor 610 may be a graphics processing unit (GPU). Image processing methods may, at least in part, be implemented by program instructions configured for execution on one of, or parallel execution on two or more of, such GPUs. The GPU(s) may implement one or more application program interfaces (APIs) that permit programmers to invoke the functionality of the GPU(s).

System memory 620 may be configured to store program instructions and/or data readable by the electronic processor 610. System memory 620 may be implemented using suitable memory technology, such as static random access memory (SRAM), synchronous dynamic RAM (SDRAM), nonvolatile/Flash-type memory, or other types of memory. In the illustrated embodiment, program instructions and data implementing desired functions, such as those described above for various embodiments, are shown stored within system memory 620 as program instructions 625 and data storage 635, respectively. In some embodiments, program instructions and/or data may be stored upon a non-transitory computer-readable medium or on media separate from system memory 620 or computer system 600. For example, the non-transitory computer readable medium may include a storage disc such as a CD, DVD, or Blue Ray disc, or a flash drive that may be coupled to the computer system 600 via the I/O device 650. Moreover, in some embodiments, the database 645 that is accessible via the network 640 may store, among other things, document data, document section data, user sharable document-display template configurations, and project assignment data.

In some embodiments, the bus 630 may be configured to coordinate traffic between the electronic processor 610, system memory 620, network interface 640, and peripheral devices, for example, the database 645, via the input/output device(s) 650. In some embodiments some or all of the functionality of the bus 630, such as an interface to system memory 620, may be incorporated directly into electronic processor 610.

Network interface 640 may be configured to allow data to be exchanged between computer system 600 and other devices attached to a network, such as other computer systems, the database 645, or between nodes of computer system 600. The network interface 640 may support communication via wired, optical, or wireless networks.

Input/output devices 650 may include one or more of a display terminal, a touch screen, a keyboard, a mouse, scanning devices, voice or optical input devices, or other devices suitable for entering or retrieving data by the computer system 600. Multiple input/output devices 650 may be present in computer system 600 or may be distributed on various nodes of computer system 600. In some embodiments, an input/output device may interact with computer system 600 through a wired or wireless connection, such as over network interface 640.

Those skilled in the art will also appreciate that, while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-readable medium or a portable article to be read by an appropriate drive, various examples of which are described above. In some embodiments, instructions stored on a computer-readable medium separate from computer system 600 may be transmitted to computer system 600 via transmission media or signals such as electrical, electromagnetic, or digital signals, conveyed via a communication medium such as a network and/or a wireless link. Various embodiments may further include receiving, sending or storing instructions and/or data implemented in accordance with the foregoing description upon a computer-readable medium. Accordingly, the present embodiments may be practiced with other computer system configurations.

The various systems and methods as illustrated in the figures and described herein represent example embodiments of methods and systems. The methods and systems may be implemented in software, hardware, or a combination thereof. The order of method may be changed, and various elements may be added, reordered, combined, omitted, modified, etc.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

Various features and advantages of the disclosure are set forth in the following claims.

We claim:

1. A control system for a predictive medical monitor, the control system comprising:
    an electronic processor; and
    a memory communicatively coupled to the electronic processor, the memory storing:
        a guide model including a non-linear predictive model for estimating a guiding first patient parameter;
        a deep neural network, the deep neural network including:
            an input layer configured to receive the guiding first estimated patient parameter;
            a plurality of hidden layers, wherein each hidden layer comprises a respective plurality of artificial neurons, each artificial neuron in a hidden layer being configured to perform a linear or nonlinear transformation on output of at least one artificial neuron from an adjacent layer in the deep neural network; and
            an output layer configured to receive at least one output from a hidden layer;
    the memory further storing instructions that when executed by the electronic processor configure the electronic processor to:
        receive patient input data;
        input the patient input data into the guide model and generate the guiding first estimated patient parameter based on the guide model and the patient input data; and
        input the patient input data and the guiding first estimated patient parameter into the deep neural network input layer and generate the second estimated patient parameter based on the deep neural network, the patient input data, and the guiding first estimated patient parameter.

2. The control system of claim 1, wherein the guide model is a physiological model.

3. The control system of claim 1, wherein the guide model is a modified Bergman Minimal Model.

4. The control system of claim 1, wherein the guiding first estimated patient parameter includes a first estimated future glucose level and the second estimated patient parameter includes a second estimated future glucose level.

5. The control system of claim 1, wherein the patient input data includes a measured blood glucose level.

6. The control system of claim 1, wherein the patient input data includes an endogenous glucose production factor.

7. The control system of claim 1, wherein the patient input data includes one or both of a physical activity factor and a meal intake factor.

8. The control system of claim 1, wherein the second estimated patient parameter is utilized to determine an input parameter in a closed loop control system.

9. A method for controlling a predictive medical monitor, the method comprising:
   storing, in a memory, a guide model including a non-linear predictive model for estimating a guiding first patient parameter;
   storing, in the memory, a deep neural network, the deep neural network including:
      an input layer configured to receive the guiding first estimated patient parameter;
      a plurality of hidden layers, wherein each hidden layer comprises a respective plurality of artificial neurons, each artificial neuron in a hidden layer being configured to perform a linear or nonlinear transformation on output of at least one artificial neuron from an adjacent layer in the deep neural network; and
      an output layer configured to receive at least one output from a hidden layer; and with an electronic processor coupled to the memory:
   receiving patient input data;
   inputting the patient input data into the guide model and generating the guiding first estimated patient parameter based on the guide model and the patient input data; and
   inputting the patient input data and the guiding first estimated patient parameter into the deep neural network input layer and generating the second estimated patient parameter based on the deep neural network, the patient input data, and the guiding first estimated patient parameter.

10. The method of claim 9, wherein the guide model is a physiological model.

11. The method of claim 9, wherein the guide model is a modified Bergman Minimal Model.

12. The method of claim 9, wherein the guiding first estimated patient parameter includes a first estimated future glucose level and the second estimated patient parameter includes a second estimated future glucose level.

13. The method of claim 9, wherein the patient input data includes one or more of a measured blood glucose level, an endogenous glucose production factor, a physical activity factor, or a meal intake factor.

14. The method of claim 9, wherein the second estimated patient parameter is utilized to determine an input parameter in a closed loop control system.

15. A transitory computer-readable medium comprising instructions that when executed by an electronic processor, cause the electronic processor to:
   store, in a memory, a guide model including a non-linear predictive model for estimating a guiding first patient parameter;
   store, in the memory, a deep neural network, the deep neural network including:
      an input layer configured to receive the guiding first estimated patient parameter;
      a plurality of hidden layers, wherein each hidden layer comprises a respective plurality of artificial neurons, each artificial neuron in a hidden layer being configured to perform a linear or nonlinear transformation on output of at least one artificial neuron from an adjacent layer in the deep neural network; and
      an output layer configured to receive at least one output from a hidden layer;
   receive patient input data;
   input the patient input data into the guide model and generate the guiding first estimated patient parameter based on the guide model and the patient input data; and
   input the patient input data and the guiding first estimated patient parameter into the deep neural network input layer and generate the second estimated patient parameter based on the deep neural network, the patient input data, and the guiding first estimated patient parameter.

16. The transitory computer-readable medium of claim 15, wherein the guide model is a physiological model.

17. The transitory computer-readable medium of claim 15, wherein the guide model is a modified Bergman Minimal Model.

18. The transitory computer-readable medium of claim 15, wherein the guiding first estimated patient parameter includes a first estimated future glucose level and the second estimated patient parameter includes a second estimated future glucose level.

19. The transitory computer-readable medium of claim 15, wherein the patient input data includes one or more of a measured blood glucose level, an endogenous glucose production factor, a physical activity factor, or a meal intake factor.

20. The transitory computer-readable medium of claim 15, wherein the second estimated patient parameter is utilized to determine an input parameter in a closed loop control system.

* * * * *